(12) United States Patent
Cao et al.

(10) Patent No.: US 12,360,070 B2
(45) Date of Patent: Jul. 15, 2025

(54) IN-SITU EVALUATION METHOD AND SYSTEM FOR LOESS COLLAPSIBILITY BASED ON NON-DESTRUCTIVE TIME-DOMAIN REFLECTION TECHNOLOGY

(71) Applicants: CHINA JIKAN RESEARCH INSTITUTE OF ENGINEERING INVESTIGATIONS AND DESIGN, Co.,Ltd, Shaanxi (CN); Xi'an Jiaotong University, Shaanxi (CN)

(72) Inventors: Jie Cao, Shaanxi (CN); Jiwen Zhang, Shaanxi (CN); Zaixin Wan, Shaanxi (CN); Qingyi Mu, Shaanxi (CN); Jianguo Zheng, Shaanxi (CN); Yuanqiang Zhou, Shaanxi (CN); Peng Gao, Shaanxi (CN); Dongjing Wang, Shaanxi (CN); Shuai Liu, Shaanxi (CN); Long Zhang, Shaanxi (CN); Zhi Liu, Shaanxi (CN); Xiao Dong, Shaanxi (CN); Jiao Lin, Shaanxi (CN); Hui Li, Shaanxi (CN); Lei Ran, Shaanxi (CN); Teng Yang, Shaanxi (CN); Jian Chen, Shaanxi (CN)

(73) Assignees: CHINA JIKAN RESEARCH INSTITUTE OF ENGINEERING INVESTIGATIONS AND DESIGN Co., Ltd, Shaanxi (CN); Xi'an Jiaotong University, Shaanxi (CN)

(*) Notice: Subject to any disclaimer, the term of this patent is extended or adjusted under 35 U.S.C. 154(b) by 57 days.

(21) Appl. No.: 18/134,557

(22) Filed: Apr. 13, 2023

(65) Prior Publication Data
US 2023/0251221 A1 Aug. 10, 2023

(30) Foreign Application Priority Data

Apr. 13, 2022 (CN) .......................... 202210394637.8

(51) Int. Cl.
*G01R 27/26* (2006.01)
*G01F 23/284* (2006.01)
(Continued)

(52) U.S. Cl.
CPC ......... *G01N 27/221* (2013.01); *G01F 23/284* (2013.01); *G01N 33/246* (2013.01); *G01R 27/2676* (2013.01)

(58) Field of Classification Search
CPC .............. G01F 23/284; G01N 27/221; G01N 27/2676; G01N 33/246; G01S 13/885
See application file for complete search history.

(56) References Cited

U.S. PATENT DOCUMENTS 7,746,726 B2 * 6/2010 Fuller ...................... G01V 1/28
367/57
2004/0249609 A1 * 12/2004 Hocheng ............... G03F 7/0002
702/185

(Continued)

*Primary Examiner* — Thang X Le
(74) *Attorney, Agent, or Firm* — Lei Yu (57) ABSTRACT

An in-situ evaluation method and system for loess collapsibility based on non-destructive time-domain reflection technology, includes: calculating loess dry density and mass water content; considering loess dry density, mass water content and basic physical property indicators, and evaluating loess collapsibility in situ through mathematical models. The loess collapsibility in-situ evaluation method based on the non-destructive time domain reflectometry technology of the present invention can not only realize whether the loess has collapsibility, but also has the potential to distinguish strong, medium and slight collapsibility.

10 Claims, 6 Drawing Sheets

(51) Int. Cl.
*G01N 27/22* (2006.01)
*G01N 33/24* (2006.01)

(56) References Cited

U.S. PATENT DOCUMENTS

| | | | | |
|---|---|---|---|---|
| 2005/0274513 A1* | 12/2005 | Schultz | ............... | E21B 47/13 |
| | | | | 166/254.2 |
| 2013/0092432 A1* | 4/2013 | Crompton | ............ | G01N 33/10 |
| | | | | 174/70 R |

* cited by examiner

IN-SITU EVALUATION METHOD AND SYSTEM FOR LOESS COLLAPSIBILITY BASED ON NON-DESTRUCTIVE TIME-DOMAIN REFLECTION TECHNOLOGY

CROSS REFERENCE OF RELATED APPLICATION

The present application claims priority under 35 U.S.C. 119(a-d) to CN 202210394637.8, filed Apr. 13, 2022.

BACKGROUND OF THE PRESENT INVENTION

Field of Invention

The present invention belongs to the technical field of in-situ survey in the field of geotechnical engineering, and more particularly to an in-situ evaluation method and system for loess collapsibility based on non-destructive time-domain reflection technology.

Description of Related Arts

As a special soil with water sensitivity, loess is widely distributed in Northwest of China, accounting for about 6% of Chinese land area. With the social and economic development and national development strategy needs, the scale of infrastructure construction in the loess area is increasing day by day. When carrying out engineering construction in loess areas, accurate subsidence survey and evaluation of the site is an important prerequisite for ensuring the service performance and safety of engineering structures.

At present, there are mainly two methods for the evaluation of loess collapsibility: indoor test and field test. For the indoor test method, the original loess samples of different depths were obtained by in-situ drilling, and then the one-dimensional consolidation instrument was used in the laboratory to perform mechanical compression and water injection saturation in the state of constant water content and test the collapsibility coefficient. Finally the measured collapsibility coefficient evaluates the collapsibility of loess. Although this method is simple, it has disadvantages such as difficult and time-consuming to obtain the original sample. First of all, the process from taking undisturbed samples on site to laboratory testing will inevitably cause damage to the loess structure, which will affect the accuracy of collapsibility evaluation. Secondly, the one-dimensional compression test of indoor constant water content requires 24 hours to stabilize each level of load, which is extremely time-consuming for testing a large number of undisturbed samples in a large-area loess site.

For field test methods, it is classified into static load test and test pit immersion test. The static load test is used to determine the initial pressure of collapsibility, and the test pit immersion test is used to determine the amount of self-weight collapsibility and the lower limit depth of self-weight collapsibility. For the static load test, first excavate the test site on site, then use the loading device to pressurize and inject water and observe the settlement, and finally determine the initial pressure of the subsidence according to the pressure-settlement curve. For the immersion test of the test pit, first excavate the test pit on site and set up punctuation points, then observe the amount of collapsibility, water consumption, wet range and ground cracks during the immersion process, and finally obtain the self-weight collapsibility and limit depth of the self-weight collapsibility according to the punctuation monitoring results. Although the above two field test methods have high reliability, they have the disadvantage of high cost. This is mainly due to the need to establish a test site and support complex equipment and professional technicians for field tests.

To sum up, the existing evaluation methods for loess collapsibility have shortcomings, and it is urgent to study new methods for in-situ rapid evaluation of loess collapsibility. The in-situ rapid evaluation of loess collapsibility can be classified into three steps: Firstly, comprehensively consider the main indicators affecting loess collapsibility, and establish a mathematical model for collapsibility evaluation. Secondly, for the main indicators in the collapsibility evaluation mathematical model, the in-situ test technology is utilized for accurate testing. Finally, based on the tested indicators and the collapsibility evaluation mathematical model, the in-situ evaluation of loess collapsibility is carried out. Based on a large number of existing experiments and theoretical studies on the collapsibility of loess, dry density and mass water content are two important indicators affecting the collapsibility of loess. Soil is composed of soil particles, air and water, and dry density represents the mass of soil particles per unit volume. The greater the dry density of loess, the less the pores in the soil, and the smaller the collapsible deformation after soaking in water. Mass water content refers to the mass of water contained in the unit mass of soil particles. The greater the water content of the loess mass, the smaller the allowable humidification for the soil to reach the saturated state, and the smaller the collapsible deformation after soaking in water.

Therefore, establishing a mathematical model of loess collapsibility based on dry density and mass water content, and performing accurate in-situ tests on loess dry density and water content are an effective way to achieve in-situ rapid evaluation of loess collapsibility.

SUMMARY OF THE PRESENT INVENTION

Accordingly, in view of the shortcomings in the conventional arts, technical problems of the present invention is to provide an in-situ evaluation method and system for loess collapsibility based on non-destructive time-domain reflection technology, which can determine whether loess has collapsibility, and has a strong distinction, mode rate and slight subsidence potential.

The present invention adopts technical solutions as follows.

An in-situ evaluation method for loess collapsibility based on nondestructive time domain reflectometry, comprises steps of:

S1: testing a time-domain reflection waveform diagram of the undisturbed loess at the site layout point through non-destructive time-domain reflection technology, and obtaining the dielectric constant and conductivity of the undisturbed loess at the layout point according to the time-domain reflection waveform diagram;

S2: calculating a dry density and mass water content of the undisturbed loess at the layout point in combination with the dielectric constant, electrical conductivity and indoor calibration parameters of the undisturbed loess at the layout point obtained in step S1; and S3: considering an original loess dry density, mass water content and basic physical property indexes calculated in step S2, carrying out the in-situ evaluation of loess collapsibility through a mathematical model.

Preferably, the step S1 specifically comprises: selecting the location and number of test points according to the environment of the on-site test area; leveling the proposed test points, adopting a non-invasive probe to closely fit the leveled test points for 5-10 seconds, and adopting computer-driven time domain reflection, obtaining the time-domain reflection waveform diagram of the test point by the signal transmitting device via a non-invasive probe, and calculating the dielectric constant and conductivity of the undisturbed loess according to the time-domain reflection waveform diagram.

Preferably, the step S2 specifically comprises steps of:
S201: after drying and sieving the detrital loess retrieved from the site, arrange n groups of compacted soil samples with the same dry density and different mass and water content for indoor calibration test, n≥4, and then adopting the least square method to obtain the indoor calibration parameter a1, b1, c1, d1 values; and
S202: adopting the dielectric constant, electrical conductivity and indoor calibration parameters a1, b1, c1, and d1 of the undisturbed loess at the on-site arrangement point, obtaining the dry density and mass water content of the undisturbed loess at the on-site arrangement point.

Preferably, in the step S201, the indoor calibration test is calculated according to formulas of:

$$\sqrt{K_a}\frac{p_w}{p_d} = a_1 + b_1 w;$$

$$\sqrt{EC_b}\frac{p_w}{p_d} = c_1 + d_1 w;$$

wherein Ka is the dielectric constant of the calibration sample, ECb is the conductivity of the calibration sample, pw is the water density, pd is the calibration loess dry density, and w is the mass water content.

Preferably, in the step S202, undisturbed loess quality water content $w_f$ and loess dry density $p_{d,f}$ are calculated as follows:

$$w_f = \frac{c_1\sqrt{K_{a,f}} - a_1\sqrt{EC_{b,if}}}{\beta b_1\sqrt{EC_{b,if}} - \lambda d_1\sqrt{K_{a,f}}};$$

$$p_{d,f} = (\frac{0.9\sqrt{K_{a,f}}}{a_1 + \beta b_1 w_f} + \frac{0.1\sqrt{EC_{b,f}}}{c_1 + \lambda d_1 w_f})p_w;$$

wherein $K_{a,f}$ and $EC_{b,f}$ are respectively the dielectric constant and electrical conductivity of the undisturbed loess measured in situ at the site layout points, $EC_{b,if}$ is the electrical conductivity after adjusting the dielectric constant, $p_w$ is the water density, and β and λ, are the correction coefficients of $b_1$ and $d_1$ respectively.

Preferably, the electrical conductivity $EC_{b,if}$ after dielectric constant adjustment is:

$$\sqrt{EC_{b,if}} = (\frac{\beta b_1 c_1 - a_1\lambda d_1}{\beta b_1}\frac{p_d}{p_w} + \frac{\lambda d_1}{\beta b_1}\sqrt{K_{a,f}})$$

wherein $p_d$ is the calibrated loess dry density.

Preferably, the step S3 specifically comprises:
combining with the original loess dry density, mass water content and basic physical property indicators at the layout point, calculating the collapsibility evaluation index $K_L$ of the original loess at the layout point; based on the indoor compression results, the collapsibility evaluation index $K_L$ of the original loess at the layout point, dividing the calculated value into intervals to determine strong collapsibility, moderate collapsibility, slight collapsibility and no collapsibility.

Preferably, the collapsibility evaluation index $K_L$ is:

$$K_L = \frac{(1/p_{d,f} - 1/G_s) - w_f}{I_P}$$

wherein $G_s$ is the specific gravity of loess, and $I_p$ is the plasticity index of loess.

Preferably, when $K_L$<0.85, no collapsibility; when 0.85<$K_L$<1.26, slight collapsibility; when 1.26<$K_L$<1.90, moderate collapsibility; when $K_L$ 1.90, strong collapsibility.

Another technical solution of the present invention is to provide an in-situ evaluation system for loess collapsibility based on non-destructive time domain reflectometry, comprising:
a acquisition module configured to test the time-domain reflection waveform diagram of the undisturbed loess at the site layout point through the non-destructive time-domain reflection technology, and obtains the dielectric constant and conductivity of the undisturbed loess at the layout point according to the time-domain reflection waveform diagram;
a calculation module configured to calculate the dry density and mass water content of the undisturbed loess at the site arrangement point in combination with the dielectric constant, electrical conductivity and indoor calibration parameters of the original loess at the arrangement point obtained by the acquisition module; and
a evaluation module configured to consider the original loess dry density, mass water content and basic physical characteristics calculated by the calculation module, and perform in-situ evaluation of the loess collapsibility through a mathematical model.

Compared with the prior art, the present invention has at least the following beneficial effects:

The present invention is an in-situ evaluation method for loess collapsibility based on non-destructive time-domain reflection technology, which uses non-destructive time-domain reflection technology to test the dielectric constant and electrical conductivity of loess in situ; calculates the dry density of loess based on the tested dielectric constant and electrical conductivity and mass water content; considering the loess dry density, mass water content and basic physical property indicators, the loess collapsibility is evaluated in situ through a mathematical model. It is a fast, non-destructive, economical test with the potential to differentiate between strong, moderate, and slight degrees of collapsibility.

Furthermore, reasonable selection of the location and quantity of test points can control the distribution density of test points, thereby improving the accuracy and reliability of survey results. The leveling treatment of the proposed test point and the close fit of the non-invasive probe can make the soil and the probe better contact and reduce the structural damage of the undisturbed loess during the test process, thereby obtaining stable and accurate electromagnetic wave reflection signals. The dielectric constant and electrical conductivity of undisturbed loess are tested by time-domain reflectometry. The principle is clear, the technology is mature, and the operation is simple.

Furthermore, the indoor calibration test uses n groups (n≥4) of compacted loess to cover a large range of water content, and ensures the same soil material composition as the in-situ test, which is the ratio of the dry density and mass water content of the original loess. Calculation provides representative calibration values of parameters a1, b1, c1, d1. The dry density and mass water content of undisturbed loess are calculated by combining the dielectric constant, electrical conductivity and indoor calibration parameters of undisturbed loess. This calculation process not only utilizes the electrical properties of undisturbed loess, but also includes representative calibration parameters to ensure Calculation accuracy of density and mass water content.

Furthermore, through the calibration of dielectric constant and electrical conductivity, the relationship between dielectric constant, electrical conductivity, dry density and mass water content is established, which provides a theoretical basis for indoor calibration experiments.

Furthermore, the empirical relationship between the undisturbed loess dielectric constant, electrical conductivity, indoor calibration parameters and the undisturbed loess mass water content and dry density is established through the mass water content and dry density of the undisturbed loess, which provides a basis for calculating the undisturbed loess dry density and mass water content. theoretical basis. In addition, the above calculation formula considers the changes of loess properties during the calibration process (such as: drying, compaction, etc.) and the influence of the difference in pore water conductivity of undisturbed loess and calibrated compacted loess on the test results by introducing parameters β and λ. the accuracy of the test results.

Furthermore, the relationship between the dielectric constant and the electrical conductivity is established through the adjusted electrical conductivity, and the dielectric constant is not sensitive to the change of the conductivity of the soil pore fluid, and the electrical conductivity after the adjusted dielectric constant is used. The accuracy of calculating the mass water content of undisturbed loess is improved.

Furthermore, the collapsibility evaluation index $K_L$ is calculated by using the original loess dry density, mass water content and basic physical properties. This index not only includes the main parameters affecting the collapsibility of loess, but also is relatively simple and easy to calculate. Through the indoor compression test results (according to the specification GB 50025-2018), the calculated value of the collapsibility evaluation index $K_L$ is divided into intervals. The index $K_L$ after division maintains the consistency with the standard evaluation of the degree of collapsibility, and then increases the index $K_L$ in Operability in engineering applications.

Furthermore, through the collapsibility evaluation index $K_L$, the relationship between the degree of loess collapsibility and dry density, mass water content and basic physical property indicators (such as: specific gravity, plasticity index) is established, which provides a theoretical basis for the collapsibility evaluation index $K_L$. In addition, the calculation formula is simple and the parameters are easy to obtain, so it has strong practicability.

Furthermore, according to the indoor compression test results (according to the specification GB 50025-2018), the collapsibility evaluation index $K_L$ is divided into intervals: when $K_L<0.85$, no collapsibility; when $0.85 \leq K_L<1.26$, slight collapsibility; when $1.26 \leq K_L<1.90$, moderate collapsibility; when $K_L$ 1.90, strong collapsibility. The collapsibility evaluation index $K_L$ division interval has a clear correspondence with the indoor compression results, and has strong engineering applicability.

In summary, the in-situ rapid evaluation method of loess collapsibility based on non-destructive time-domain reflectometry has clear theory, little disturbance to soil sample structure, short test time, low cost, advanced technology and high reliability, and engineering with the advantages of strong applicability, it can become a new method of engineering survey technology in loess areas.

The technical solutions of the present invention will be described in further detail below with reference to the accompanying drawings and embodiments.

BRIEF DESCRIPTION OF THE DRAWINGS

FIG. 1 is a diagram of the non-destructive time-domain reflectometry device of the present invention, wherein

FIG. 2 is the result map of the test site 1 based on the non-destructive time-domain reflectometry technology and the drying method of the present invention, wherein

FIG. 4 is a result diagram of the test site 2 based on the non-destructive time-domain reflectometry technology and the drying method of the present invention, wherein

In the FIGS. mentioned above, 1—Time domain reflection signal transmitting device; 2.—Non-invasive probe; 3—Computer; 4—Coaxial cable; 5—Epoxy resin; 6—Probe.

DETAILED DESCRIPTION OF THE PREFERRED EMBODIMENT

The following will clearly and completely describe the technical solutions in the embodiments of the present invention with reference to the accompanying drawings in the embodiments of the present invention. Obviously, the described embodiments are some of the embodiments of the present invention, but not all of them. Based on the embodiments of the present invention, all other embodiments obtained by persons of ordinary skill in the art without making creative efforts belong to the protection scope of the present invention.

In the description of the present invention, it should be understood that the terms "comprising" and "comprising" indicate the presence of described features, integers, steps, operations, elements and/or components, but do not exclude one or more other features, Presence or addition of wholes, steps, operations, elements, components and/or collections thereof.

It should also be understood that the terminology used in the description of the present invention is for the purpose of describing particular embodiments only and is not intended to be limiting of the present invention. As used in this specification and the appended claims, the singular forms "a", "an" and "the" are intended to include plural referents unless the context clearly dictates otherwise.

It should also be further understood that the term "and/or" used in the description of the present invention and the appended claims refers to any combination and all possible combinations of one or more of the associated listed items, and includes these combinations, for example, A and/or B, may mean: A exists alone, A and B exist simultaneously, and B exists alone. In addition, the character "I" in this article generally indicates that the contextual objects are an "or" relationship.

It should be understood that although the terms first, second, third, etc. may be used in the embodiments of the present invention to describe preset ranges, etc., these preset ranges should not be limited to these terms. These terms are only used to distinguish preset ranges from one another. For example, without departing from the scope of the embodiments of the present invention, the first preset range may also be called the second preset range, and similarly, the second preset range may also be called the first preset range.

Depending on the context, the word "if" as used herein may be interpreted as "at" or "when" or "in response to determining" or "in response to detecting". Similarly, depending on the context, the phrases "if determined" or "if detected (the stated condition or event)" could be interpreted as "when determined" or "in response to the determination" or "when detected (the stated condition or event))" or "in response to detection of (a stated condition or event)".

Various structural schematic diagrams according to the disclosed embodiments of the present invention are shown in the accompanying drawings. The figures are not drawn to scale, with certain details exaggerated and possibly omitted for clarity of presentation. The shapes of various regions and layers shown in the figure and their relative sizes and positional relationships are only exemplary, and may deviate due to manufacturing tolerances or technical limitations in practice, and those skilled in the art may Regions/layers with different shapes, sizes, and relative positions can be additionally designed as needed.

The invention provides an in-situ evaluation method of loess collapsibility based on non-destructive time-domain reflection technology, which uses non-destructive time-domain reflection technology to test the dielectric constant and electrical conductivity of loess in situ; calculates the loess based on the tested dielectric constant and electrical conductivity Dry density and mass water content; considering loess dry density, mass water content and basic physical property indicators, the in-situ evaluation of loess collapsibility is carried out through mathematical models. The loess collapsibility in-situ evaluation method based on the non-destructive time domain reflectometry technology of the present invention can not only realize whether the loess has collapsibility, but also has the potential to distinguish strong, medium and slight collapsibility. The method of the invention is advanced in technology, short in time consumption, low in cost, convenient in operation, high in reliability and strong in practicability, and is a new means of engineering survey technology in loess areas.

Figure 1A:
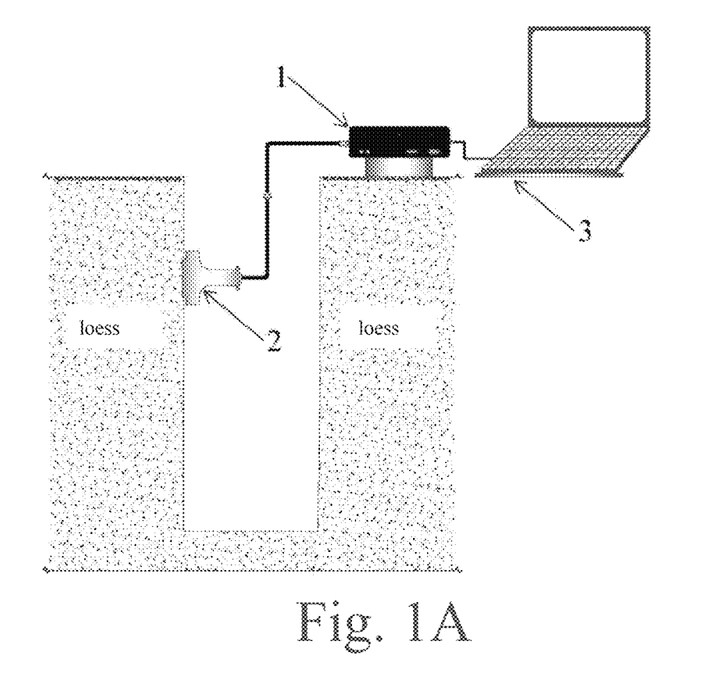
FIG. 1A is a test diagram of the non-destructive time-domain reflectometry device.
Figure 1B:
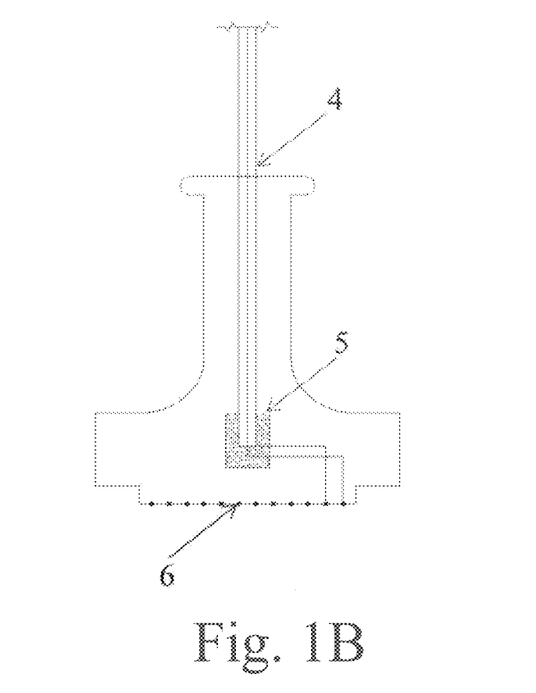
FIG. 1B is a contour diagram of a non-invasive probe.
Figure 1C:
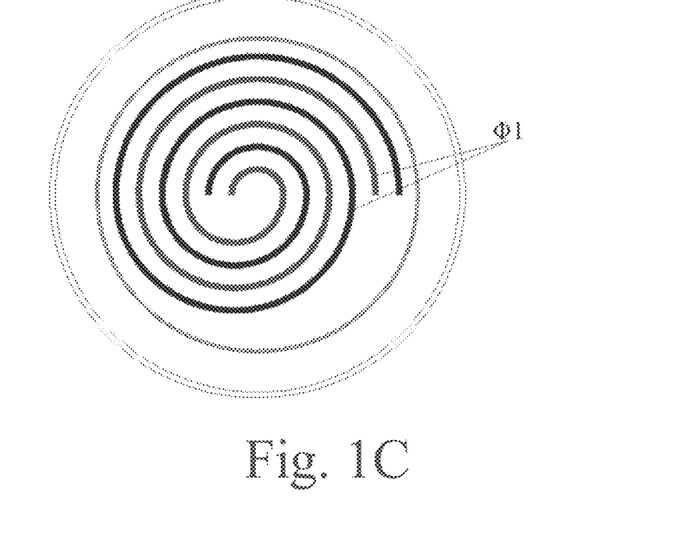
FIG. 1C is a diagram showing a probe plane layout in a non-invasive probe.

An in-situ evaluation method of loess collapsibility based on non-destructive time domain reflectometry in the present invention comprises the following steps:

S1. Test the time-domain reflection waveform diagram of the undisturbed loess at the site by non-destructive time-domain reflection technology, and then obtain the dielectric constant and conductivity of the undisturbed loess at the arrangement point;

Please refer to FIG. 1, the non-invasive probe 2 is connected with the computer through the time domain reflection signal transmitting device 1, and the time domain reflection signal transmitting device 1 is electrically connected with the probe 6 of the non-invasive probe 2 through the coaxial cable 4, coaxial The end of the cable 4 is provided with epoxy resin 5, and the probe 6 is a two-pin non-destructive probe. The probe uses a copper conductor with a width of 1 mm and a thickness of 0.02 mm. The distance between the centers of the two copper conductors is 3 mm.

Utilize the time-domain reflection signal transmitter 1 and the non-invasive probe 2 to test the time-domain reflection waveform diagram of the undisturbed loess on site, and calculate the dielectric constant and electrical conductivity of the undisturbed loess through the computer 3, specifically:

S101. According to the complexity of the engineering geological conditions in the field test area, refer to the survey method of field drilling to test the collapsibility (according to the specification GB 50025-2018), reasonably select the location and number of test points under the corresponding engineering geological conditions;

S102. Perform leveling treatment on the proposed test point, and then make the non-invasive probe closely fit the leveled test point;

S103. After bonding for 5-10 seconds, use a microcomputer to drive the time-domain reflection signal transmitter, obtain the time-domain reflection waveform diagram of the test point through a non-invasive probe, and then calculate the dielectric constant and conductivity of the undisturbed loess;

wherein after each test is completed, the residual loess on the non-invasive probe is removed with a dry cotton cloth.

After each test is completed, the same mass of loess is taken at the non-invasive probe test site, and finally loess with a total weight of about 10-15 kg is obtained for indoor calibration.

S2. Calculate the dry density and mass water content of the undisturbed loess at the site arrangement point in combination with the dielectric constant, electrical conductivity and indoor calibration parameters a1, b1, c1, and d1 of the undisturbed loess at the arrangement point;

Combining the permittivity, conductivity and indoor calibration parameters a1, b1, c1, d1 of the undisturbed loess at the site layout points, the dry density and mass water content of the undisturbed loess are calculated using the empirical model, as follows:

S201. After drying and sieving the detrital loess retrieved from the site, arrange n groups (n≥4) of compacted soil samples with the same dry density and different mass water content, and perform indoor calibration tests according to formulas (1) and (2), and then use the least square method to obtain the indoor calibration parameters a1, b1, c1, d1 values:

$$\sqrt{K_a}\frac{p_w}{p_d} = a_1 + b_1 w \quad (1)$$

$$\sqrt{EC_b}\frac{p_w}{p_d} = c_1 + d_1 w \quad (2)$$

wherein $K_a$ is the dielectric constant of the calibration sample, $EC_b$ is the conductivity of the calibration sample, $p_w$ is the water density, $p_d$ is the calibration loess dry density, w is the mass water content, and $a_1$, $b_1$, $c_1$, $d_1$ are calibration parameters;

S202. Considering the difference in electrical conductivity between the undisturbed loess pore water at the site test point and the indoor calibrated compacted loess pore water, as well as the change of loess properties before and after the calibration test, the dielectric constant and electrical conductivity of the undisturbed loess at the site layout points and the indoor calibration parameters $a_1$, $b_1$, $c_1$, $d_1$, combined with formulas (1) and (2), the empirical calculation formulas (3) and (4) for the dry density and mass water content of the undisturbed loess at the site layout point are obtained:

$$w_f = \frac{c_1 \sqrt{K_{a,f}} - a_1 \sqrt{EC_{b,if}}}{\beta b_1 \sqrt{EC_{b,if}} - \lambda d_1 \sqrt{K_{a,f}}} \quad (3)$$

$$p_{d,f} = (\frac{0.9\sqrt{K_{a,f}}}{a_1 + \beta b_1 w_f} + \frac{0.1\sqrt{EC_{b,f}}}{c_1 + \lambda d_1 w_f}) p_w \quad (4)$$

wherein $w_f$ and $p_{d,f}$ are the undisturbed loess mass water content and loess dry density calculated after the in-situ test of the site layout points respectively, $K_{a,f}$ and $EC_{b,f}$ are respectively the undisturbed loess dielectric constant and electrical conductivity of the in-situ test of the site layout points, and constant adjusted conductivity, $\beta$ and $\lambda$, are correction factors for $b_1$ and $d_1$, respectively. The purpose of the correction coefficient $\beta(0.5\sim1.3)$ is to eliminate the influence of the change of loess properties (such as: drying) caused by the calibration process. The purpose of the correction coefficient $\lambda(0\sim1)$ is to eliminate the influence of the difference in pore water conductivity between undisturbed loess and calibrated compacted loess.

In addition, the calibration parameter $a_1$ ranges from 0.7 to 1.8, and $b_1$ ranges from 7.5 to 11; since the value of $a_1$ is usually around 1, no correction is made. The calibration parameter $c_1$ is the conductivity parameter related to the dry loess, which has little change in the in-situ and calibration process, so it will not be adjusted.

The empirical calculation of $EC_{b,if}$ is as follows:

$$\sqrt{EC_{b,if}} = (\frac{\beta b_1 c_1 - a_1 \lambda d_1}{\beta b_1} \frac{p_d}{p_w} + \frac{\lambda d_1}{\beta b_1} \sqrt{K_{a,f}}) \quad (5)$$

S3. Considering the original loess dry density, mass water content and basic physical property indicators, the in-situ evaluation of loess collapsibility is carried out through a statistical mathematical model.

Considering the original loess dry density, mass water content and basic physical properties, the mathematical model is used to quickly evaluate the collapsibility of the original loess at the site layout points, specifically:

S301. Combined with the dry density, mass water content and basic physical properties of the undisturbed loess at the site layout point, use formula (6) to calculate the collapsibility evaluation index $K_L$ of the undisturbed loess at the layout point:

$$K_L = \frac{(1/p_{d,f} - 1/G_s) - w_f}{I_p} \quad (6)$$

wherein $G_s$ is the specific gravity of loess, and $I_p$ is the plasticity index of loess;

S302: Based on the indoor compression results, according to the strong collapsibility, moderate collapsibility, slight collapsibility and no collapsibility determined by the specification (GB 50025-2018), the collapsibility evaluation index $K_L$ of the undisturbed loess at the layout point is calculated. Interval division.

When $K_L<0.85$, no collapsibility;
when $0.85 \leq K_L<1.26$, slight collapsibility
When $1.26 \leq K_L<1.90$, moderate collapsibility;
When $K_L \geq 1.90$, strong collapsibility.

According to another embodiment of the present invention, an in-situ evaluation system for loess collapsibility based on lossless time-domain reflectometry is provided, which can be used to implement the above-mentioned in-situ evaluation method for loess collapsibility based on lossless time-domain reflectometry, Specifically, the loess collapsibility in-situ evaluation system based on non-destructive time domain reflectometry includes an acquisition module, a calculation module and an evaluation module;

wherein the acquisition module tests the time-domain reflection waveform diagram of the undisturbed loess at the site arrangement point through the non-destructive time-domain reflection technology, and obtains the dielectric constant and electrical conductivity of the original loess at the arrangement point according to the time-domain reflection waveform diagram;

the calculation module calculates the dry density and mass water content of the undisturbed loess at the site arrangement point in combination with the dielectric constant, electrical conductivity and indoor calibration parameters of the original loess at the arrangement point obtained by the acquisition module; and the evaluation module considers the original loess dry density, mass water content and basic physical characteristics calculated by the calculation module, and performs in-situ speed evaluation on the collapsibility of loess through a mathematical model.

In order to make the purpose, technical solutions and advantages of the embodiments of the present invention clearer, the technical solutions in the embodiments of the present invention will be clearly and completely described below in conjunction with the drawings in the embodiments of the present invention. Obviously, the described embodiments It is a part of embodiments of the present invention, but not all embodiments. The components of the embodiments of the invention generally described and illustrated in the drawings herein may be arranged and designed in a variety of different configurations. Accordingly, the following detailed description of the embodiments of the invention provided in the accompanying drawings is not intended to limit the scope of the claimed invention, but merely represents selected embodiments of the invention. Based on the embodiments of the present invention, all other embodiments obtained by persons of ordinary skill in the art without creative efforts fall within the protection scope of the present invention.

In order to further illustrate an in-situ rapid evaluation method for loess collapsibility based on non-destructive time-domain reflectometry in the present invention, the present invention specifically selects two sites for verification as examples for analysis and description.

Site 1: A typical exploration well in an exploration project in Jingyang County, Shaanxi Province. The depth of the exploratory well is 20.0 m, and testers conduct tests along the depth of the well at intervals of 1.0 m. Among them, the 10.0 m~14.0 m is the ancient soil layer and contains more calcareous concretions, and the leveling effect is poor, so no test was carried out. During the implementation process, testers conduct test applications according to the specific implementation mode of the present invention.

S1. Use a crane to enter the exploration well at a depth of 1.0 m, and level the test points on the left and right sides of the well wall; then, after making the non-invasive probe closely fit the leveled test points for 5 to 10 seconds, use a micro The computer-driven time-domain reflection signal transmitter is tested through a non-invasive probe, and then the time-domain reflection waveform diagram of the test point is obtained. It should be noted that after each test, use a dry cotton cloth to remove residual loess from the test end of the non-intrusive probe. Further, after completing the test at the same depth, the staff descended with the crane and performed the same test at intervals of 1.0 m until the depth of the exploratory well was 20.0 m. Among them, the exploration wells with a depth of 10.0 m-14.0 m are ancient soil layers and contain many calcareous concretions, and the test was not carried out due to the poor leveling effect of the test surface. Therefore, a total of 32 non-destructive time-domain reflection waveform tests were carried out along the depth of 0 m-20.0 m in the exploratory well, and finally the dielectric constant and electrical conductivity of 32 groups of undisturbed loess were calculated. In addition, after each test, undisturbed loess blocks and detrital loess with a size of about 150 mm×150 mm×150 mm were collected at the non-invasive probe test site. Among them, the undisturbed loess block is used for indoor drying method to verify the accuracy of non-destructive time-domain reflectometry in testing loess dry density and mass water content, and for indoor compression tests to verify the applicability of the mathematical model for evaluating loess collapsibility. Indoor calibration test and test of basic physical parameters.

Figure 2A:
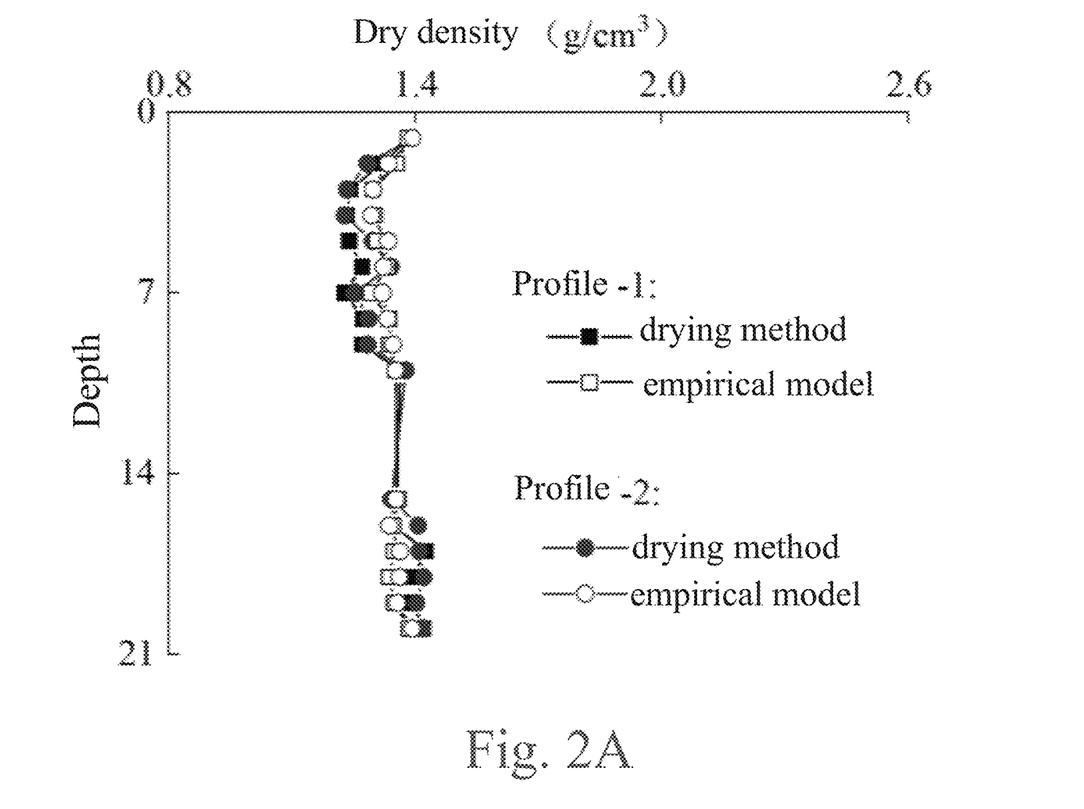
FIG. 2A is the dry density.
Figure 2B:
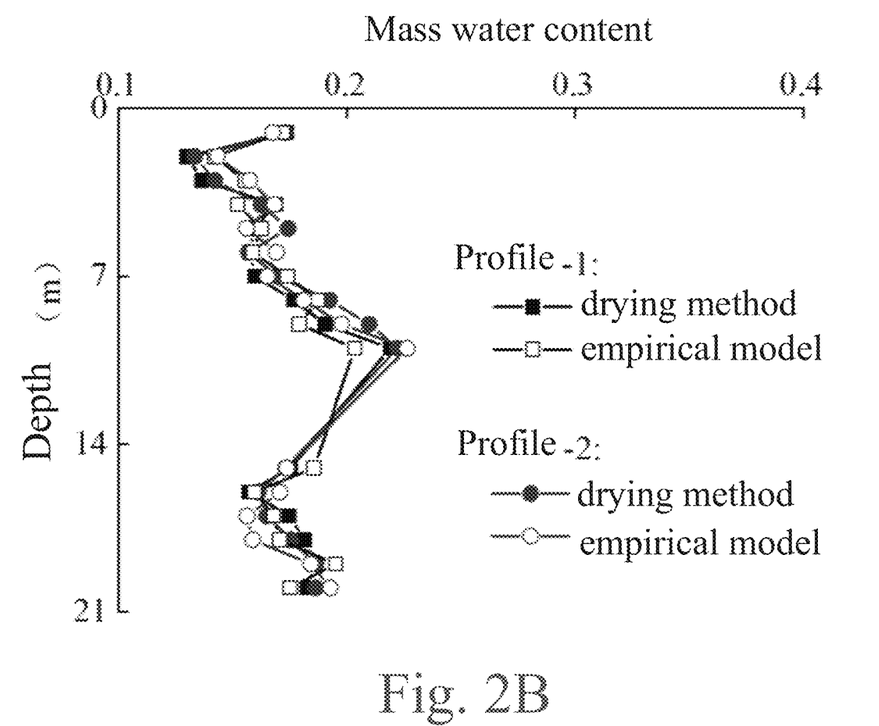
FIG. 2B is the mass water content.

S2. After drying and sieving the detrital loess retrieved from the site, configure groups of compacted soil samples with the same dry density and different mass water content for indoor calibration test, and then use the least square method to obtain the values of the parameters $a_1$, $b_1$, $c_1$ and $d_1$ are 1.3644, 10.789, 0.0784, and 0.6237 respectively; further, the mass water content and water content of the undisturbed loess at the site layout points are calculated by using the dielectric constant, electrical conductivity and indoor calibration parameters $a_1$, $b_1$, $c_1$, and $d_1$ of the site layout points. dry density. Among them, using formulas (3) and (5) to calculate the mass water content of the undisturbed loess at the site layout point, the values of $\beta$ and $\lambda$, are 0.990 and 0.481, respectively. Subsequently, the dry density of the undisturbed loess at the site layout points was calculated using the calculated mass water content of undisturbed loess and formula (4). It is worth noting that in this case, in order to illustrate the feasibility of the present invention more clearly, the results of dry density and mass water content of loess obtained by indoor drying method and non-destructive time domain reflectometry were compared, as shown in FIG. 2.

Figure 3:
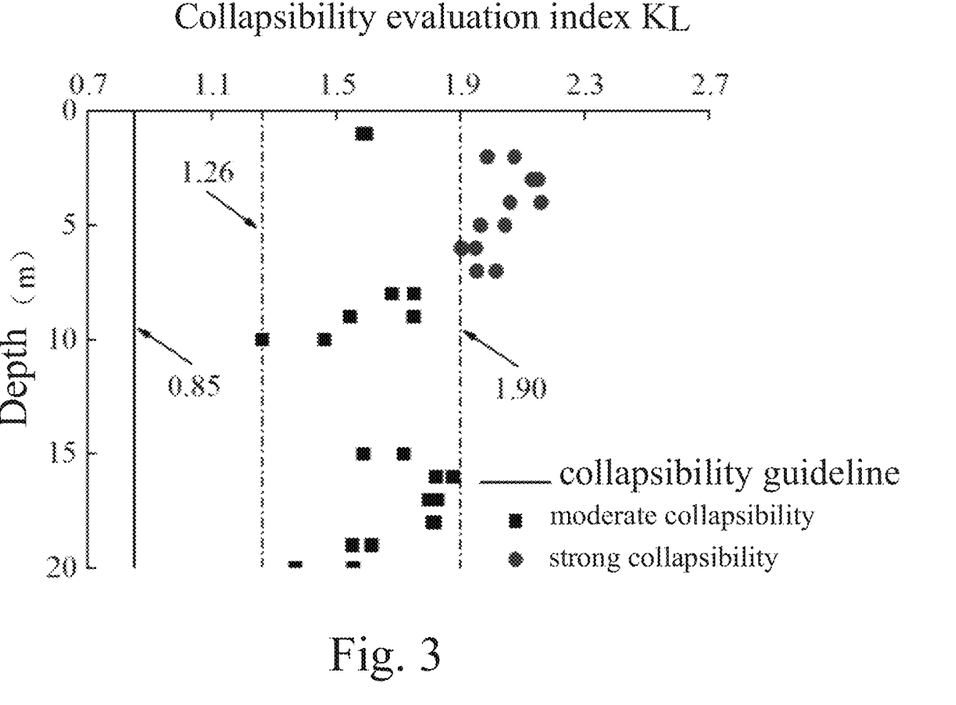
FIG. 3 is the comparison chart of site 1 judging the collapsibility results based on the method of the present invention and the indoor compression test.

S3. The collapsibility evaluation index $K_L$ of undisturbed loess at different layout points is calculated according to formula (6) in combination with loess dry density, mass water content and basic physical property indicators (such as: plasticity index $I_p$ and specific gravity $G_s$). Then, according to the $K_L$ value, it corresponds to strong collapsibility ($K_L \geq 1.90$), moderate collapsibility ($1.26 \leq K_L \leq 1.90$), slight collapsibility ($0.85 \leq K_L < 1.26$) and no collapsibility ($K_L < 0.85$). The collapsibility of the undisturbed loess at the arrangement point is evaluated. It is worth noting that in this case, in order to illustrate the feasibility of the present invention more clearly, the indoor compression results were compared with the prediction results of the loess collapsibility evaluation mathematical model, as shown in FIG. 3.

Site 2: A foundation pit site in Xixian New District, Xi'an City, Shaanxi Province. The foundation pit site is 25.0 m long and 15.0 m wide. In this test, two measuring lines with an interval of 4.0 m are selected along the excavation surface of the foundation pit. Each measuring line is 16.0 m long and the test point interval is 1.0 m. A total of 32 tests were carried out. test. The tester performs the test application according to the specific implementation mode of the present invention.

S1. Leveling the test points in the selected area. Then, after the non-invasive probe is closely attached to the leveled test point for 5-10 seconds, a microcomputer-driven time-domain reflection signal transmitter is used for testing through the non-invasive probe, and then the time-domain reflection waveform of the test point is obtained. picture. It should be noted that after each test, the residual loess on the non-intrusive probe should be removed with a dry cotton cloth. Furthermore, 16 tests were carried out for each measuring line, and finally a total of 32 sets of time-domain reflection waveforms were obtained in the selected area, and then the dielectric constant and conductivity of 32 sets of undisturbed loess were calculated. In addition, after each test, undisturbed loess blocks and detrital loess with a size of about 150 mm×150 mm×150 mm were collected at the non-invasive probe test site, and finally 32 undisturbed loess blocks with a total weight of about 10~15 kg of detrital loess. Among them, the undisturbed loess block is used for indoor drying method to verify the accuracy of non-destructive time-domain reflectometry for testing loess dry density and mass water content, and for indoor compression tests to verify the applicability of the mathematical model for evaluating loess collapsibility. Indoor calibration test and test of basic physical parameters.

Figure 4A:
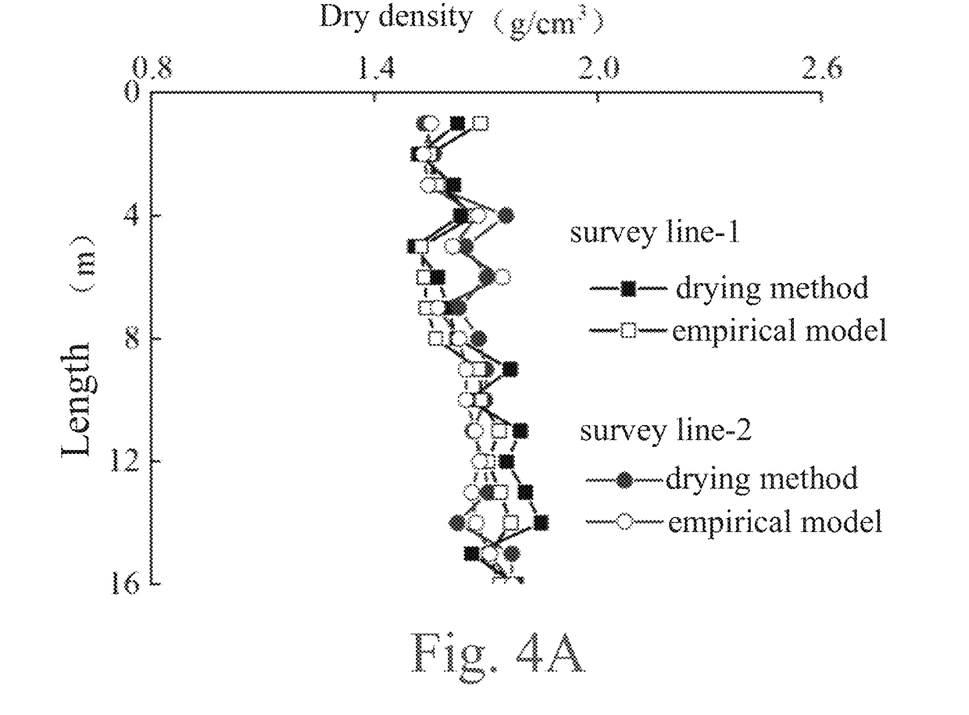
FIG. 4A is the dry density.
Figure 4B:
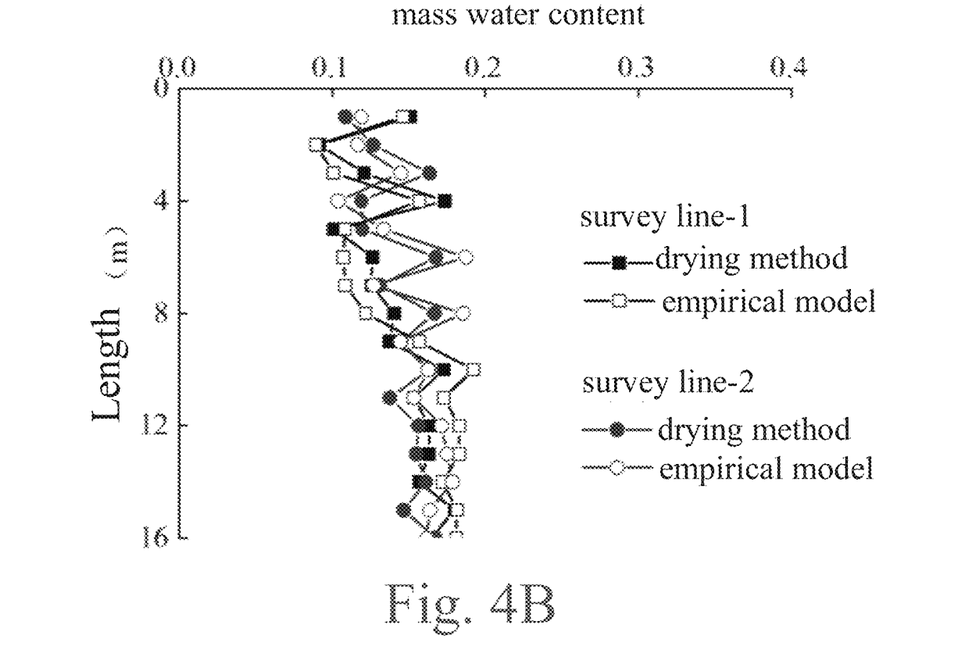
FIG. 4B is the mass water content.

S2. After drying and sieving the detrital loess retrieved from the site, configure groups of compacted soil samples with the same dry density and different quality and water content, and carry out indoor calibration according to formulas (1) and (2), and then use the least squares method The obtained values of parameters $a_1$, $b_1$, $c_1$, and $d_1$ are 1.1611, 10.465, 0.0873, and 0.6562, respectively. Further, the mass water content and dry density of the undisturbed loess at the site arrangement points are calculated by using the permittivity, electrical conductivity and indoor calibration parameters $a_1$, $b_1$, $c_1$, and $d_1$ of the undisturbed loess at the site arrangement points. Among them, using formulas (3) and (5) to calculate the mass water content of the undisturbed loess at the site layout point, the values of $\beta$ and $\lambda$, are 0.841 and 0.046, respectively. Subsequently, the dry density of undisturbed loess at site layout points was calculated by using the mass water content of undisturbed loess and formula (4). It is worth noting that in this case, in order to illustrate the feasibility of the present invention more clearly, the results of dry density and mass water content of loess obtained by indoor drying method and non-destructive time domain reflectometry were compared, as shown in FIG. 4.

Figure 5:
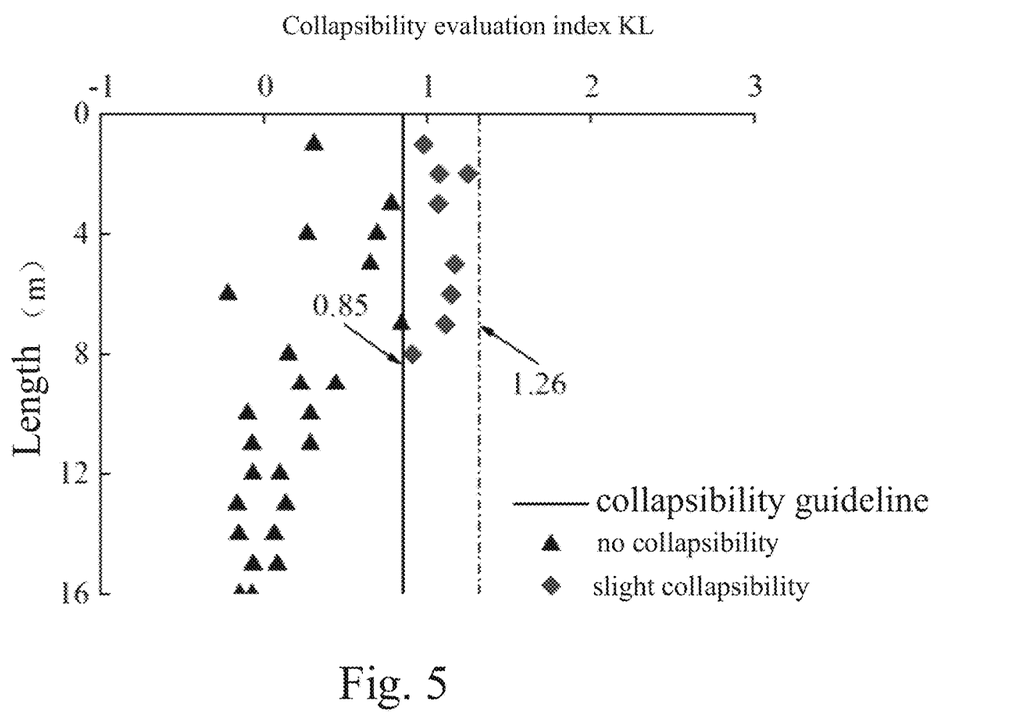
FIG. 5 is a comparison chart of site 2 judging the collapsibility based on the method of the present invention and the indoor compression test.

S3. The collapsibility evaluation index KL of undisturbed loess at different layout points is calculated according to formula (6) in combination with loess dry density, mass water content and basic physical property indicators (such as: plasticity index Ip and specific gravity $G_s$). Then, according to the $K_L$ value, it corresponds to strong collapsibility ($K_L \geq 1.90$), moderate collapsibility ($1.26 \leq K_L < 1.90$), slight collapsibility ($0.85 \leq K_L < 1.26$) and no collapsibility ($K_L < 0.85$). The collapsibility of the undisturbed loess at the arrangement point is evaluated. It is worth noting that in this case, in order to illustrate the feasibility of the present invention more clearly, the indoor compression results were compared with the prediction results of the loess collapsibility evaluation mathematical model, as shown in FIG. 5.

To sum up, a method and system for in-situ evaluation of loess collapsibility based on lossless time-domain reflectometry in the present invention has characteristics as follows.

(1) Compared with the traditional loess collapsibility survey technology, the in-situ rapid evaluation method of loess collapsibility based on non-destructive time-domain reflectometry has the advantages of less disturbance to the soil sample structure, short time, low cost, advanced technology and High reliability and other advantages.

(2) The present invention uses non-destructive time-domain reflectometry technology to test the dry density and mass water content of loess in situ. The technology is mature and advanced, the test time is short, and the reliability is high. Furthermore, the equipment is easy to operate, easy to carry, and strongly adaptable to the site.

(3) The loess collapsibility evaluation mathematical model adopted in the present invention has good prediction effect, less required parameters and strong practicability.

(4) An in-situ rapid evaluation method of loess collapsibility based on non-destructive time-domain reflectometry technology of the present invention can not only realize the judgment of whether the loess has collapsibility, but also has the ability to distinguish strong, medium and slight collapsibility (standard GB 50025-2018) potential.

(5) The evaluation method of the present invention enriches the means of engineering survey technology in loess areas, has strong engineering popularization and applicability, and can become a new means of engineering survey technologies in loess areas.

Those skilled in the art should understand that the embodiments of the present application may be provided as methods, systems, or computer program products. Accordingly, the present application may take the form of an entirely hardware embodiment, an entirely software embodiment, or an embodiment combining software and hardware aspects. Furthermore, the present application may take the form of a computer program product embodied on one or more computer-usable storage media (including but not limited to disk storage, CD-ROM, optical storage, etc.) having computer-usable program code embodied therein.

The present application is described with reference to flowcharts and/or block diagrams of methods, apparatus (systems), and computer program products according to embodiments of the present application. It should be understood that each procedure and/or block in the flowchart and/or block diagram, and combinations of procedures and/or blocks in the flowchart and/or block diagram can be realized by computer program instructions. These computer program instructions may be provided to a general purpose computer, special purpose computer, embedded processor, or processor of other programmable data processing equipment to produce a machine such that the instructions executed by the processor of the computer or other programmable data processing equipment produce a means for realizing the functions specified in one or more steps of the flowchart and/or one or more blocks of the block diagram.

These computer program instructions may also be stored in a computer-readable memory capable of directing a computer or other programmable data processing apparatus to operate in a specific manner, such that the instructions stored in the computer-readable memory produce an article of manufacture comprising instruction means, the instructions The device realizes the function specified in one or more procedures of the flowchart and/or one or more blocks of the block diagram.

These computer program instructions can also be loaded onto a computer or other programmable data processing device, causing a series of operational steps to be performed on the computer or other programmable device to produce a computer-implemented process, thereby The instructions provide steps for implementing the functions specified in the flow chart flow or flows and/or block diagram block or blocks.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An in-situ evaluation method for loess collapsibility based on nondestructive time domain reflectometry, comprising steps of:
   S1: testing a time-domain reflection waveform diagram of the undisturbed loess at the site layout point through non-destructive time-domain reflection technology, and obtaining a dielectric constant, electrical conductivity and indoor calibration parameters of an undisturbed loess at a layout point according to the time-domain reflection waveform diagram;
   S2: calculating a dry density and mass water content of the undisturbed loess at the layout point in combination with the dielectric constant, electrical conductivity and indoor calibration parameters of the undisturbed loess at the layout point obtained in step S1; and
   S3: performing an in-situ evaluation of loess collapsibility through a mathematical model based on inputs of an original loess dry density, mass water content and basic physical property indexes calculated in step S2.

2. The in-situ evaluation method for loess collapsibility based on nondestructive time domain reflectometry, as recited in claim 1, wherein the step S1 specifically comprises: selecting a location and number of test points according to the environment of an on-site test area; leveling the test points selected, adopting a non-invasive probe to closely fit the test points leveled for 5-10 seconds, and adopting computer-driven time domain reflection, obtaining the time-domain reflection waveform diagram of the test point by a signal transmitting device via the non-invasive probe, and calculating the dielectric constant and electrical conductivity of the undisturbed loess according to the time-domain reflection waveform diagram.

3. The in-situ evaluation method for loess collapsibility based on nondestructive time domain reflectometry, as recited in claim 1, wherein the step S2 specifically comprises steps of:

S201: after drying and sieving the detrital loess retrieved from the site, arrange n groups of compacted soil samples with the same dry density and different mass and water content for indoor calibration test, n≥4, and then adopting the least square method to obtain the indoor calibration parameter a1, b1, c1, d1 values; and S202: adopting the dielectric constant, electrical conductivity and indoor calibration parameters a1, b1, c1, and d1 of the undisturbed loess at the on-site arrangement point, obtaining the dry density and mass water content of the undisturbed loess at the on-site arrangement point.

4. The in-situ evaluation method for loess collapsibility based on nondestructive time domain reflectometry, as recited in claim 3, wherein in the step S201, the indoor calibration test is calculated according to formulas of:

$$\sqrt{K_a}\frac{p_w}{p_d} = a_1 + b_1 w;$$

$$\sqrt{EC_b}\frac{p_w}{p_d} = c_1 + d_1 w;$$

wherein Ka is the dielectric constant of the calibration sample, ECb is the conductivity of the calibration sample, pw is the water density, pd is the calibration loess dry density, and w is the mass water content.

5. The in-situ evaluation method for loess collapsibility based on nondestructive time domain reflectometry, as recited in claim 3, wherein in the step S202, undisturbed loess quality water content $w_f$ and loess dry density $p_{d,f}$ are calculated as follows:

$$w_f = \frac{c_1\sqrt{K_{a,f}} - a_1\sqrt{EC_{b,jf}}}{\beta b_1 \sqrt{EC_{b,jf}} - \lambda d_1 \sqrt{K_{a,f}}};$$

$$p_{d,f} = (\frac{0.9\sqrt{K_{a,f}}}{a_1 + \beta b_1 w_f} + \frac{0.1\sqrt{EC_{b,f}}}{c_1 + \lambda d_1 w_f})p_w;$$

wherein $K_{a,f}$ and $EC_{b,f}$ fare respectively the dielectric constant and electrical conductivity of the undisturbed loess measured in situ at the site layout points, $EC_{b,jf}$ is the electrical conductivity after adjusting the dielectric constant, $p_w$ is the water density, and β and λ are the correction coefficients of $b_1$ and $d_1$ respectively.

6. The in-situ evaluation method for loess collapsibility based on nondestructive time domain reflectometry, as recited in claim 5, wherein the electrical conductivity $EC_{b,jf}$ after dielectric constant adjustment is:

$$\sqrt{EC_{b,jf}} = (\frac{\beta b_1 c_1 - a_1 \lambda d_1}{\beta b_1}\frac{p_d}{p_w} + \frac{\lambda d_1}{\beta b_1}\sqrt{K_{a,f}});$$

wherein $p_d$ is the calibrated loess dry density.

7. The in-situ evaluation method for loess collapsibility based on nondestructive time domain reflectometry, as recited in claim 1, wherein the step S3 specifically comprises:

combining with the original loess dry density, mass water content and basic physical property indicators at the layout point, calculating the collapsibility evaluation index $K_L$ of the original loess at the layout point; based on the indoor compression results, the collapsibility evaluation index $K_L$ of the original loess at the layout point, dividing the calculated value into intervals to determine strong collapsibility, moderate collapsibility, slight collapsibility and no collapsibility.

8. The in-situ evaluation method for loess collapsibility based on nondestructive time domain reflectometry, as recited in claim 7, wherein the collapsibility evaluation index $K_L$ is:

$$K_L = \frac{(1/p_{d,f} - 1/G_s) - w_f}{I_P}$$

wherein $G_s$ is the specific gravity of loess, and $I_p$ is the plasticity index of loess.

9. The in-situ evaluation method for loess collapsibility based on nondestructive time domain reflectometry, as recited in claim 7, wherein when $K_L$<0.85, no collapsibility; when 0.85≤$K_L$<1.26, slight collapsibility; when 1.26≤$K_L$<1.90, moderate collapsibility; when $K_L$≥1.90, strong collapsibility.

10. An in-situ evaluation system for loess collapsibility based on non-destructive time domain reflectometry, comprising:

an acquisition module configured to test a time-domain reflection waveform diagram of an undisturbed loess at a site layout point through the non-destructive time-domain reflection technology, and obtains a dielectric constant and conductivity of the undisturbed loess at the layout point according to the time-domain reflection waveform diagram;

a calculation module configured to calculate the dry density and mass water content of the undisturbed loess at the site arrangement point in combination with the dielectric constant, electrical conductivity and indoor calibration parameters of the original loess at the arrangement point obtained by the acquisition module; and an evaluation module configured to perform an in-situ evaluation of the loess collapsibility through a mathematical model based on inputs of an original loess dry density, mass water content and basic physical property indexes calculated by the calculation module.

* * * * *